United States Patent [19]
Grotz

[11] Patent Number: 5,968,078
[45] Date of Patent: Oct. 19, 1999

[54] STABILIZER FOR HUMAN JOINTS

[75] Inventor: R. Thomas Grotz, San Francisco, Calif.

[73] Assignee: Ultraortho, Inc., San Francisco, Calif.

[21] Appl. No.: 09/104,814

[22] Filed: Jun. 25, 1998

Related U.S. Application Data

[63] Continuation of application No. 08/712,635, Aug. 21, 1996, Pat. No. 5,782,865.
[60] Provisional application No. 60/002,794, Aug. 25, 1995.

[51] Int. Cl.$^6$ .................................................. A61B 17/04
[52] U.S. Cl. ............................ 606/232; 606/72; 606/104
[58] Field of Search ............................... 606/232, 72, 73, 606/76, 77, 104

[56] References Cited

U.S. PATENT DOCUMENTS 5,380,334  1/1995  Torrie et al. ............................ 606/232

FOREIGN PATENT DOCUMENTS 2671717  7/1992  France .................................. 606/232

*Primary Examiner*—Gary Jackson
*Attorney, Agent, or Firm*—Townsend and Townsend and Crew LLP

[57] ABSTRACT

This invention pertains to a medical device for securing bodily tissues to bone, and more particularly to a triangular shaped joint stabilizer comprising sharpened, toothed bone anchors that are forcibly spread into the bone by a central plug.

23 Claims, 2 Drawing Sheets

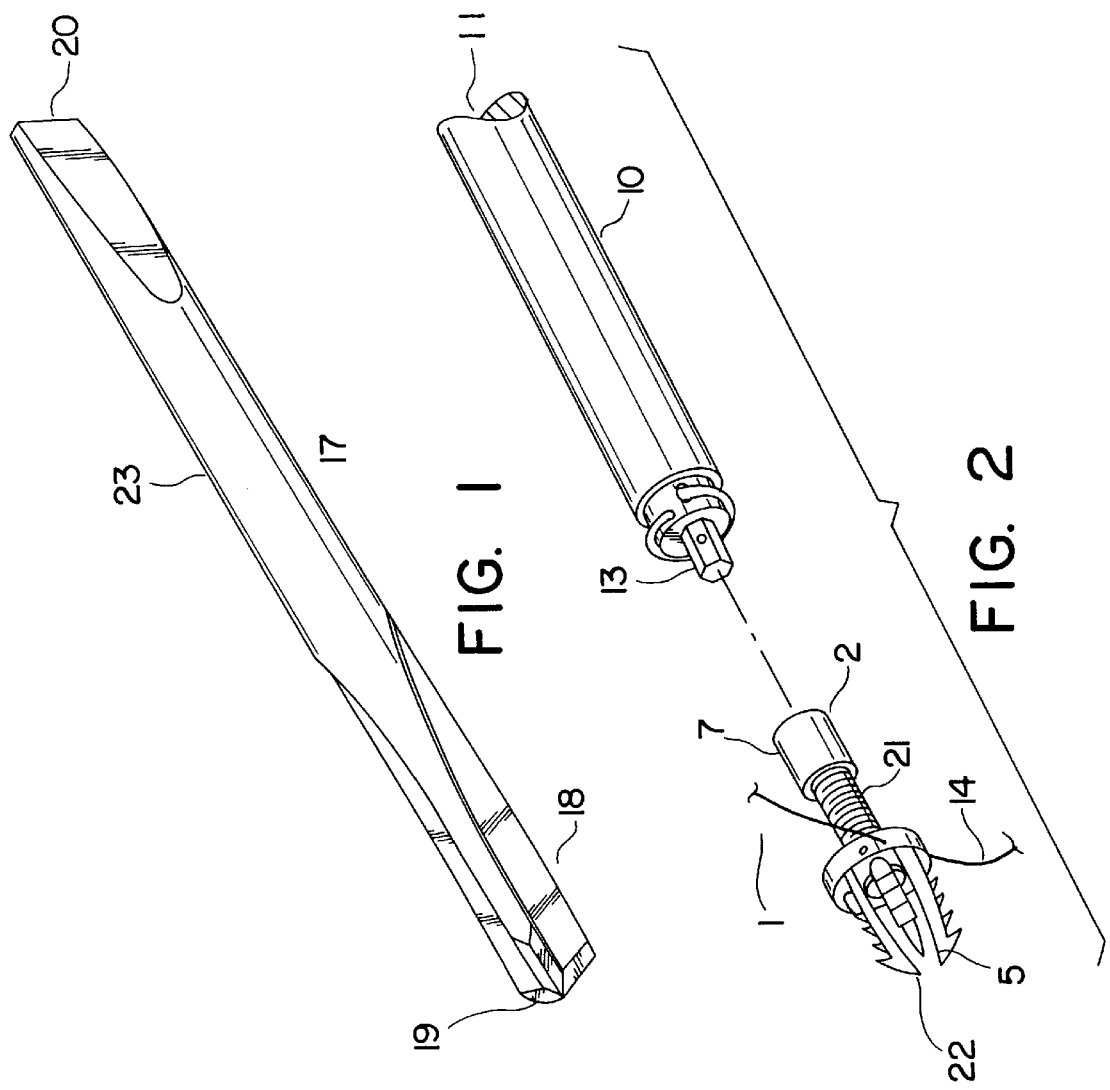

STABILIZER FOR HUMAN JOINTS

CROSS REFERENCE TO RELATED APPLICATIONS

This application is a continuation of U.S. patent application Ser. No. 08/712,635, filed Aug. 21, 1996, now U.S. Pat. No. 5,782,865, which is a continuation-in-part of U.S. provisional application No. 60/002,794, filed Aug. 25, 1995.

FIELD OF THE INVENTION

This invention pertains to an improved medical device for securing soft body tissues to bone, and more particularly to a joint stabilizer comprising toothed bone anchors that are forcibly spread into the bone by a central plug. The specific improvements include the ability of the invention to gather soft tissue, to retain the tissue by multiple sutures, and to secure itself to bone by distal penetration of its moveable legs.

BACKGROUND

Currently there are various staples and anchor devices for attaching soft tissue to bone. None of the tissue stabilizing devices known to the inventor provide multiple sutures to be anchored, distally expand in contrast to proximal expansion or an equal expansion along their long axis, and collect soft tissue into the receiving hole of the bone. Alternative devices also suffer from low pull-out strength, a lack of adequate suture attachment sites, a failure to assist the surgeon in positioning soft tissue into contact with bone prior to suturing to maximize bonding of the soft tissue to bone (tissue gathering capabilities), and an overall difficulty in physically handling the devices during surgery.

Generally, injury to joints such as the shoulder and knee involve the tearing or separation of ligaments from their natural position on the bone. The injury leads to a chronic instability in the joint which requires surgical intervention. Modernly, the surgery involves use of one or more arthroscopic devices. These devices include surgical cannulas through which a camera or surgical device are passed. The arthroscopic methods involve less iatrogenic trauma to the patient than previous methods and predict a faster recovery.

In brief, the surgical procedures involve visualization and localization of the damage, preparation of the bone surface, implantation of a soft tissue anchor, and suturing of the tissue to the bone to tighten up the joint and restabilize it. By tightly contacting the ligament or other soft tissue to a properly prepared bone surface, the two materials bond during the healing process.

SUMMARY OF THE INVENTION

It is an objective of this invention to provide a device with an increased pull-out strength relative to currently available joint stabilizers, and to provide a device which affords the capacity to use multiple sutures for gathering up a maximum amount of soft tissue for rejoining with bone. This invention further provides for sharp bone anchors and ligament combs that direct and draw ligaments, tendons, or other soft tissues to the bone to better facilitate and maximize the amount of soft tissue that is placed in contact with the bone during the reparative steps.

The present invention is generally characterized by first and second parts wherein the first part is a central body forming a hollow core or opening which defines a longitudinal axis, said body having laterally positioned (horizontal) proximal and distal faces, with bone anchors extending along the long axis from the distal face, said anchors symmetrically positioned about the face and in a first position that is internally angled from the vertical to form a triangular shape (toward the center of the horizontal), each anchor having at least one bone engaging tooth and sharp ends to penetrate or gather soft tissue; and, wherein the second part of said system comprises a central plug positioned within the hollow core of the central body, and said plug having a generally elongate shape forming a head, a shank and a distal portion where the head forms a receptor for receiving a complementary driver device, the shank connects the head to the distal portion of the peg, and where the core is threaded, the central peg has an optionally threaded shank wherein the shank diameter and thread complement and engage threads of the central core, and the distal portion of the plug has a diameter that permits it to contact the bone anchors when the anchors are in the first internal lateral (unexpanded) position, said distal portion placing an increasing lateral force on the anchors as the central peg is driven by impact force along its elongate axis or is threaded by torque force through the threaded hollow core whereby the lateral force moves the bone anchors into a second external lateral (expanded) position in which the teeth penetrate into bone that is about equal to or outside of the diameter of the central body.

Preferred embodiments of the central body include devices as described above where the distal face of the central body further comprises ligament combs that are rigid projections that extend laterally (distally) from the face and where the combs are symmetrically positioned about the face. The central body is preferably circular as in the form of a washer, and preferably includes suture fasteners that are optionally hollow passages cut through the central body.

Preferred embodiments of the central plug include embodiments where the head of the central plug sits nearly flush with or is internal to the proximal face of the central body. A preferred head shape includes a receptacle for receiving a driver that is capable of transmitting impact along the elongate (vertical) axis or torque force in instances when the shank and core are complementarily threaded.

The invention further includes a system having as one of its components the above-described stabilizer and further includes a driver that is generally an elongate rod having a head, a shank and a distal portion. The head is formed to receive impact force. The shank is of a diameter that fits within an arthroscopic cannula and is of a length that permits the head and distal portion to be delivered through the cannula. The distal portion can be designed to mate with the receptor formed by the head of the central plug. The driver is optionally modified to include a snap fitting that complements the head of the peg to prevent accidental separation during surgery. The snap fitting may be based on a detent and dimple connection or wire and groove connection.

Alternatively, the driver can be contained within a holder that is designed to prevent slippage of the driver from the central plug. By controlling the distance the driver is permitted to travel, one can prevent over-striking or impacting of the central peg. The driver/holder assembly would resemble a hollow cylinder which would function as the holder where the driver is internal to the cylinder and has a safety stop or projection to control its extension upon impact. This assembly can also be used as an inserter/suture organizer which can be used to direct the stabilizer to its target site.

The invention further includes a system having as one of its components the above-described stabilizer and further including a trocar or drill bit for penetrating bone. The trocar or drill bit having a generally elongate or rod shape comprising a head, a shank and a distal portion. The head of the trocar is shaped to receive an axial impact force and transfer said force evenly along the length of the trochar device to the distal portion. In the case of a drill bit, the head is formed to be connected to a drill chuck. The shank is of a diameter that fits within an arthroscopic cannula and has a length that permits the head and distal portions to extend beyond the cannula. The distal portion of the trocar comprises a sharpened end having multiple cutting edges that match the number of bone anchors of the central body and having size that will create a concavity that complements the external shape of the stabilizer when its bone anchors are in the first position.

BRIEF DESCRIPTION OF THE DRAWINGS

FIG. 1. is a side view of a trocar that matches a joint stabilizer having three bone anchors.

FIG. 2 is side view of the stabilizer made according to this invention and a driver.

DESCRIPTION OF THE PREFERRED EMBODIMENT

A soft tissue stabilizer 1 in accordance with this invention is described in FIGS. 2–5. The stabilizer is preferably made of biocompatible or physiologically inert materials. Such materials include titanium and its alloys, stainless steel, and cobalt based alloys. Bioabsorbable materials can also be used and include aliphatic polyesters of alpha-hydroxy acid derivatives as described in Rokkanen, P.V. (1991) "Absorbable Materials in Orthopedic Surgery," *Annals of Med.* 23:109–115.

The precise dimensions of the stabilizer can vary with its intended use and the patient size. The following overall dimensions are suited for the shoulder and knee joints of an adult human of average size, and can be modified for specific patients or uses. Along the axis defined by the core 15 of the central body 3, reaching from the proximal face of the body 3 to the distal ends of the bone anchors 6, the device is from 2 to 20 mm. The width of the stabilizer is from 2 to 15 mm. The thickness of the central body 3 between the distal and proximal faces is preferably from 0.8 to 4.0 mm.

The central body 3 can be circular, or a polygon of three or more sides. The central core 15 can be circular or a polygon. Circular forms are preferred. The proximal surface of body 3 is preferably flat or concave to minimize any surface extending above the cortex of the bone in situations where such surface might interfere with function, as in joints.

Figure 3:
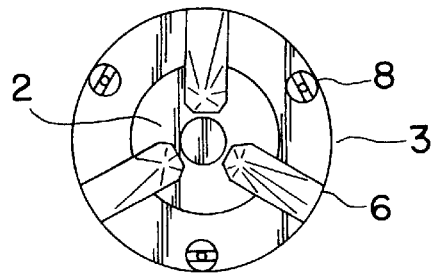
FIG. 3 is a view of the distal end of the stabilizer.
Figures 4A, 4B:
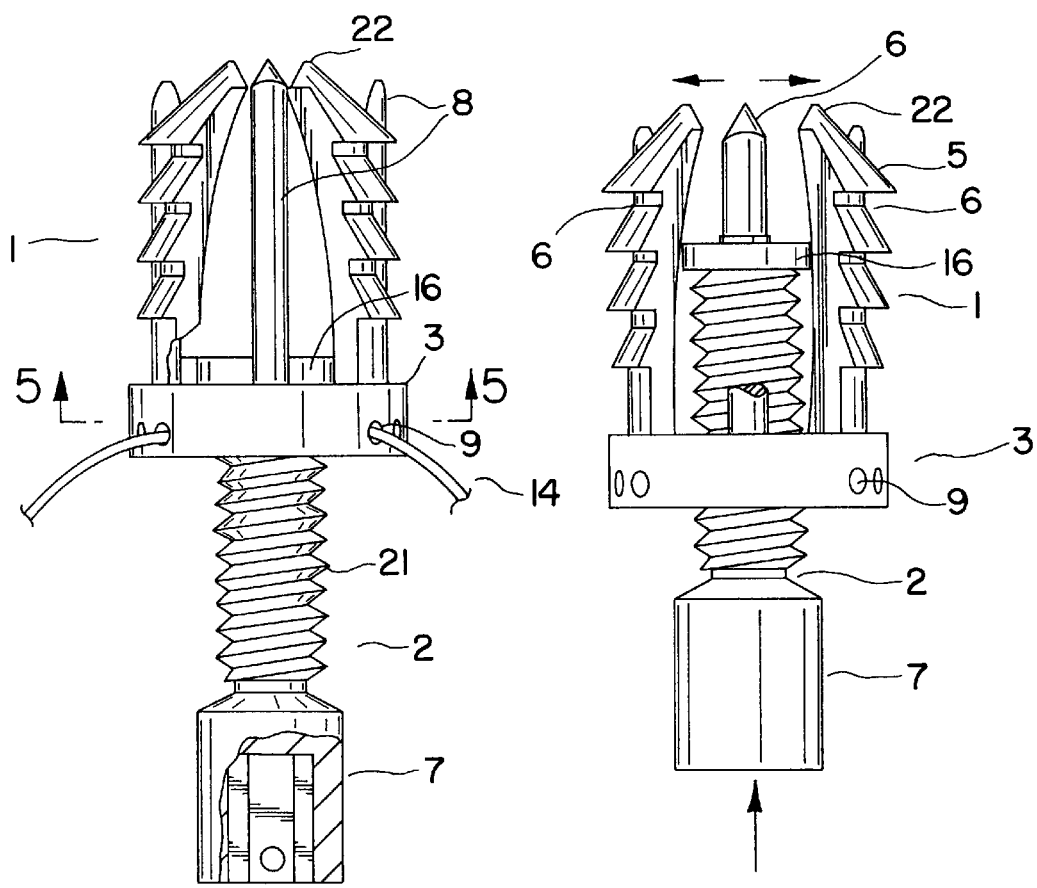
FIG. 4A is a side view of the stabilizer of FIG. 2 with the bone anchors in the first position.
FIG. 4B is a side view of the stabilizer of FIG. 2 with the bone anchors in the second position.

The distal surface of the body 3 in FIG. 2 has three bone anchors 6 as shown in side view in FIG. 4A. It is preferred that the body 3 have from 2–4 anchors. The bone anchors 6 are attached to the central body 3 by a variety of conventional means, including welding, casting from a single mold, screwing, riveting, or pressure-fitted together by means of a tapered insert into a hole. The anchors are tapered to a sharp point and have at least one bone engaging tooth 5, and preferably several teeth 5. The teeth are attached to the outer surface of the anchors to be directed into bone when the anchors are expanded. The teeth 5 act as barbs to increase the pull-out strength of the stabilizer. Where multiple teeth 5 are present, they may increase in size as they are positioned more distal from the central body 3. The teeth 5 are preferably tapered to sharpened points that are able to penetrate the interior matrix (cancellous portion) of the bone, specially prepared with the matching kit drill.

The anchors 6 are preferably symmetrically positioned about the central body 3. When the distal ends 22 of anchors 6 are in the first internal lateral position, see FIG. 4A, they are parallel to or angled internal to the longitudinal axis, the preferred internal angle being 8 to 15 degrees. When in the internal lateral position, the teeth 5 are at or within the cylindrical, axially extending region defined by the body 3. As the distal ends 22 of the anchors 6 are moved to their second or external, more lateral position, the distance between the ends 22 and the long axis of the stabilizer 1 will increase to place the teeth 5 at or just beyond the cylindrical axially extending region defined by the body 3, see FIG. 4B.

In addition to having bone anchors 6, the body 3 may optionally bear ligament combs 8, which are elongate pins that are positioned between the anchors 6, preferably symmetrically about the anchors 6. As shown in FIG. 4A, the combs 8 are approximately the same length as the anchors 6. The combs are rigid and tapered to a sharp end for gathering ligament and other soft tissue, and for penetrating the bone.

Figure 5:
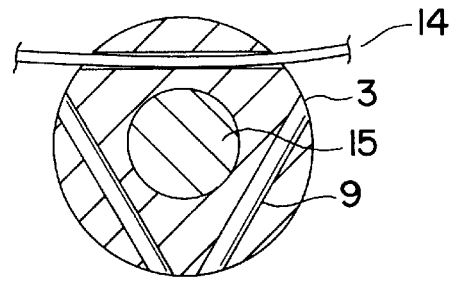
FIG. 5 is a cross-sectional view of the central body along line 5—5 of FIG. 4A.

The central body 3 may optionally comprise suture fasteners 9 which are depicted in FIGS. 4 and 5 as internal, laterally directed passages cut or drilled out of the central body 3. Alternatively, the fasteners could be holes drilled along the longitudinal axis through the distal and proximal faces of the central body 3, or loop-like means or hook-like means which could be cut into or mounted to the central body 3. Prior to implantation of the stabilizer 1, the suture threads can be attached or threaded through the central body 3. Alternatively, the suture fasteners might be located on the central plug 2 or bone anchors 6.

Positioned within the central core 15 is a central plug 2. The central plug 2 is an elongate structure comprising a head 7 that is designed to receive a driver device—termed a central plug driver 10. If the plug 2 is pressure fitted into the hollow core 15, the head 7 has a generally symmetric surface for receiving impact force and transmitting the force equally down the length of the plug 2. The head 7 can be flat or slightly concave to prevent slippage of the driver 10 during use. When the central plug 2 is threaded, as in FIG. 4A, and positioned by torque force, the head 7 can be single or multiply slotted, or cut out to form a socket such as a hexagonal socket for receiving a complementary central plug connector 13.

The shank 21 of the central plug 2 is either smooth or threaded. The nature of the thread is not critical and 8-36 inch thread is useful and provides suitable control. As the central plug 2 is moved from a first upper position to a second lower position, the distal end of the central plug 16 is designed to spread or force the bone anchors 6 from a first internal lateral position, as depicted in FIG. 4A, to a second external lateral position, as depicted in FIG. 4B.

The diameter of the head 7 is not critical. The diameter can be larger or smaller or equal to the diameter of the shank 21. To facilitate assembly, the head 7 may preferably be of sufficient size to pass through the opening 15 or the central body 3. In a similar vein, and although the diameter of the distal end 16 of the central plug 2 of FIG. 4A is larger than the central opening 15, it would be apparent to those of skill that the diameter of end 16 is not critical and could be equal or slightly smaller than the opening 15 to accommodate assembly.

The bone surface is optionally prepared with a trocar 17 that has a cutting surface that matches the stabilizer 1 (see FIG. 1). More particularly, the trocar 17 is comprised of a head 20 connected to an elongate shank 23 which is connected to distal end 19 having cutting edges 18. This distal end 19 has an external size and configuration to create a concavity in bone that complements the external configuration of the central body 3 when its bone anchors 6 are in the first position. The concavity created by the trocar 17 should be the same size or just slightly smaller than the external size of the stabilizer 1 when in the position of FIG. 4A. The trocar 17 can be made of any material that can be sterilized, be formed into a cutting edge 18, and withstand the impact force needed to penetrate bone. Metal alloys such as stainless steel are preferred. The overall diameters of the trocar are not critical and need only be long enough to reach into the joint and extend outside a suitable distance for receiving the impact force, or for drill attachment to a chuck. An overall length of eight to twelve inches with an outside diameter of 0.5 to 1.5 cm is suitable for the anticipated uses.

Alternatively, the bone surface may be prepared with a drill bit that creates a hole in the bone large enough to receive the tissue stabilizer. The cut hole can be either straight or angled to walls to form a Morse taper.

The central plug driver 10 is illustrated in FIG. 2 and is designed to transfer either axillary impact force or torque force to the central plug head 7 to move the central plug 2 from its first to its second position. If impact force is used to move the central plug 2, the central plug connector 13 is a blunt tapered end or a flat end. If torque force is used to move the central plug 2, the central plug connector 13 can be flat or be formed into a socket or a hex shape or a cut to shape that will fit into a slot or Phillip's type of head. The handle 11 comprises an elongate shank and a head that is shaped to either receive impact force and transfer that force equally down the shank to the connector 13 such as a flat surface, or shaped to facilitate frictional grasping for application of torque force such as a flattened surface for twisting between the thumb and forefinger or a spherical ball. The overall dimensions of the driver are the same as those provided above for the trocar 17.

The central plug driver 10 may be used to position the stabilizer 1 into the concavity created by the trocar 17. To facilitate the positioning of the stabilizer through tissue to bone, the driver and device can be held together by the sutures or the driver 10 can be snap fitted to the stabilizer 1. The means for snap fitting is not critical. Typical examples include tension wire and groove fittings or dimple, detent fittings. The strength of the fitting should be such that accidental separations are minimized while deliberate separations are possible after insertion into bone without inadvertent pull-outs. Pull-out strengths can be measured according to Shall, et al., "Soft Tissue Reconstruction in the Shoulder: Comparison of Suture Anchors, Absorbable Staples and Absorbable Tacks, *Amer. J. Sports Med.,* 22:715–718 (1994) or Hecker, et al., "Pull-Out Strength of Suture Anchors for Rotator Cuff and Bankart Lesion Repairs," *Amer. J. of Sports Med.,* 21:874–879 (1993). The FDA has also issued recent guidelines.

It should be noted that the claimed stabilizer expands at its distal end. This is in contrast to other expanding anchors that expand equally along their longitudinal axis or at their proximal end as an arrowhead shape. Distal expansion provides improved pullout strength by maximizing overlying bone contact.

Multicomponent kits are also a part of this invention. The kits will include at a minimum the tissue stabilizing device as described herein as a first component. Other components include the drill, sutures and the inserter/suture organizer.

The surgical procedures for which the device is particularly suited are repairs to the shoulder and knee joints such as reconstructing anterior cruciate ligament (ACL) deficiencies and for repairing dislocating shoulders and torn rotator cuffs. However, the stabilizer is universally applicable to most efforts which warrant reattachment of soft tissue to bone. The following, brief description of surgical procedures are not intended to be the only way the inventions described herein could be used and are presented for illustration purposes and not by way of limitation.

For repairing shoulder injuries, the patient is prepared for surgery and within a sterile field two or three incisions are made. The first incision is anterior superior on the shoulder 1 cm lateral to the anterior glenohumeral joint line, and 1 cm beneath the inferior acromion's palpable cortex. This incision is 1.0 cm in length and vertically positioned. The next two incisions are 0.5 cm in length and horizontal to the body axis. The second incision is posterior superior, 1 cm lateral to the posterior glenohumeral joint line, 1 cm beneath the acromion palpable cortex. The third incision is lateral to the acromion just posterior to the greater tuberosity of the humerus and supraspinatus attachment, 1 cm beneath the inferior acromion palpable cortex. All incisions are made just to the depth of superficial subcutaneous tissue. The newer arthroscopic devices allow the posterior incision to be omitted.

The arthroscopic camera equipment is positioned by driving a sharp trocar inside a cannula to the synovium, and then a blunt trocar through the synovium. A scope cannula is positioned through either the lateral or posterior incision. A pressure pump cannula is then posteriorly or laterally positioned and the stabilizer cannula containing a smooth trocar is placed into the anterior glenohumeral joint. The joint is examined to study the effusion and synovium before arthroscopic fluid enters (unless pre-infusion is needed for instrument insertion). One next washes out the joint with Ringer's lactate and checks the labrum for tears and/or detachment. Good practice includes looking at the biceps tendon and inferior cuff from the posterior or lateral position. This process allows one to identify any Bankart lesion or other anterior inferior glenohumeral ligament maladies, or any capsular laxity.

The joint repair is conceptualized to locate the point of stabilizer placement that will maximize joint stability. Selecting a stabilizer with a threaded or smooth cylindrical central plug, one assembles, if not already assembled, the two parts of the stabilizer so that the central plug is approximately 50% of the way into the central body and just contacting the bone anchors. The stabilizer is then snap fitted on the central plug driver, or fixed by the inserter/suture organizer. The tissue to be captured and re-attached is revisualized with usual attention paid to the anterior inferior shoulder and inside the joint. The surgeon then probes the pathology with a smooth trocar through the cannula.

The glenoid rim is prepared either by using a sharp, pointed trocar, by pre-drilling to expose bone, by burring, or by use of the star-tipped trocar as in FIG. 1. The stabilizer is placed into the anterior shoulder through an accommodating cannula. The stabilizer is then used to pierce the tissue inside the joint, "teasing it" onto the anchors and optimal combs, and the stabilizer is then driven into bone while the assistant surgeon holds the arm up against the glenoid. Next, the central plug is tightened down to expand the bone anchors into their second position for extra fixation security.

In cases where sutures are required, the sutures are attached to the suture fasteners prior to insertion and used in conventional ways to tie additional soft tissue to the bone. A suture-passing device can be used here.

In the final step, the surgeon checks the joint motion, implant and joint stability, and rules out any impingement of the implant against mobile surfaces.

For repairs to the knee, one follows an analogous protocol. Two or three incisions are made to a patient's knee after appropriate external site preparation steps are completed. The first incision is at the femorotibial joint line 1 cm above the tibial plateau palpable surface just medial to the patella tendon, 1 cm in length, and horizontal. The second incision is horizontal, 0.5 cm in length, and along the joint line just lateral to the patella tendon. The third incision is about 3 cm above the top of the patella superolaterally. The incision depths are to subcutaneous tissue. The third incision can usually now be omitted with newer arthroscopic equipment.

The arthroscopic equipment is positioned inferolaterally using the sharp trocar to the synovium and blunt trocar through the synovium. The surgeon then places a stabilizer cannula along the inferior medial 1 cm incision through the skin, and then vertically into the intercondylar notch along the medial parapatellar tendon with a smooth tipped trocar inside a cannula. A pressure pump cannula is then placed above and lateral to the patella, about 3 cm superior to the upper patella border, or attached to new scope equipment. Good practice mandates that all four compartments of the knee joint are then examined to study the effusion and synovium before arthroscopic fluids enter. Care is taken to avoid iatrogenic cartilage injury.

The joint is then washed out with Ringer's lactate, checking the anterior cruciate ligament for location of tear, degree of strand compromise, concomitant ligament conduit attenuation, and remnant attachment tissue qualities.

To place the stabilizer in its optimal position, one must first conceptualize the goals of repair to identify the location on the condyle where the stabilizer will provide maximum security and adequate (isometric) function. The stabilizer is then prepared as above for the shoulder. The pathology is then reprobed to locate tissue to be captured. Most common is damage to the femoral ACL remnant, in repair cases. The stabilizer also provides for secure fixation in reconstruction cases, wherein autografts or allografts are used.

The surgeon then prepares the concavity for implanting the stabilizer by a limited synovectomy, burr notchplasty, and then by exposing bone inside the notch at the inner lateral femoral condyle. A pointed tipped trocar may be used if the upper ligamentous remnant is sufficient, or otherwise the bone can be prepared with the trocar of FIG. 1 used by impact or by drill.

The surgeon then places the joint stabilizer into the anteromedial knee wound through an accommodating cannula. One pierces the anterior cruciate ligament fibers toward the mid and upper section of the remaining attenuated or torn conduit for distal to proximal ACL fixation, teasing as many strands and fibers onto the implant device as can be gathered. The ligament combs are designed to help organize the strands, and the combination of toothed bone anchors and ligament combs or pins will comb, or align, the remaining anterior cruciate fibers before bringing them up to and into bone.

The stabilizer is then driven into the prepared concavity, while the knee is flexed at about 30 degrees, and the assistant surgeon holds the tibia up towards the femur. The central plug is then impacted down, thus expanding the prongs inside the bone, locking the stabilizer into place. The optional use of sutures completes the repair. The surgeon ties the knots if pre-secured using bioabsorbable (#1) PDS suture, or with the suture of choice, and checks the joint clinically for stability and impingement.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A soft tissue anchor device for securing soft tissue to bone, the device comprising:
    a central body defining an opening, the body having proximal and distal faces that extend in a lateral direction;
    at least two bone anchors extending from the distal face and having distal ends, the distal ends being movable between a first internal and a second external lateral position, each anchor having at least one bone engaging tooth;
    means for engaging and gathering soft tissue; and,
    a central plug positioned within the opening of the central body and including a head, a shank and a distal portion;
        wherein the shank is movable through the opening of the central body so that the distal portion of the plug is positionable between a first upper and second lower axial position; and,
        wherein the distal portion of the plug is sized to contact the bone anchors so that when the distal portion of the plug is moved into the second axial position, the distal ends of the bone anchors are moved towards the second lateral position.

2. The device of claim 1 wherein the means for engaging and gathering soft tissue comprises ligament combs that are rigid pins that extend axially from the distal face.

3. The device of claim 1 wherein the means for engaging and gathering soft tissue comprises sharp distal ends on the bone anchors and each engaging tooth is configured to engage and gather soft tissue.

4. The tissue anchor device of claim 1 wherein the central plug is integral with the tissue anchor device.

5. The tissue anchor device of claim 4 wherein the central plug is pressure fitted within the opening.

6. The tissue anchor device of claim 4 wherein the central plug is threaded within the opening.

7. The device of claim 1 wherein the central body is circular.

8. The device of claim 1 wherein said body defines a cylindrical axially extending region, said bone anchors lying substantially completely within the region when the distal ends of the anchors are in the first lateral position with substantial portions of the teeth lying outside the cylindrical region when said distal ends of the anchors are in the second lateral position.

9. The device of claim 1 wherein the number of bone anchors is three.

10. The device of claim 1 wherein the opening of the central body and the shank of the central peg are frictionally mated without threads using smooth surfaces to position the central peg along the axis defined by the opening.

11. The device of claim 10 wherein the head forms a receptor for receiving a driving tool.

12. The device of claim 1 wherein the head of the central plug sits flush with or is internal to the proximal face of the central core when in the second position.

13. The device of claim 1 wherein the device is made of a bioabsorbable material.

14. The device of claim 1 wherein the device is comprised of stainless steel alloy, titanium alloy and cobalt alloys.

15. A method of attaching soft tissue to a bone, the method comprising:

provinding a soft tissue anchor device including a bone engaging surface;

providing a bore within the bone;

gathering soft tissue upon the bone engaging surface;

placing the bone engaging surface and gathered tissue within the bore; and engaging the bone engaging surface with the bone.

16. A soft tissue anchor device configured to be placed within a bore defined within a bone for securing soft tissue to the bone, the device comprising:

a central body having an opening defined therein, the central body comprising a distal face;

at least two bone anchors extending from the distal face, each anchor including at least one bone engaging tooth, each of the at least two anchors being configured to move from an internal position to an external position relative to the central body; and means for engaging and gathering soft tissue;

wherein when the means for engaging and gathering soft tissue engages soft tissue and the device is within the bore, some tissue is gathered into the bore; and wherein when the at least two bone anchors are moved from the internal position to the external position when the device is within the bore, the device is secured within the bore.

17. The tissue anchor device of claim 16 wherein each anchor further comprises a sharp distal end that terminates proximally into a bone engaging tooth configured to engage and gather tissue.

18. The tissue anchor device of claim 16 further comprising means for spreading the anchors outwardly, the means for spreading the anchors outwardly comprising a central plug positioned within the opening.

19. The tissue anchor device of claim 18 wherein the central plug is pressure fitted within the opening.

20. The tissue anchor device of claim 18 wherein the central plug is threaded within the opening.

21. A soft tissue anchor device in accordance with claim 16 wherein the means for engaging and gathering soft tissue comprises a sharp distal tip at a distal end of each of the at least two bone anchors.

22. A soft tissue anchor device in accordance with claim 16 wherein the means for engaging and gathering soft tissue comprises the at least one bone engaging tooth included on the at least two bone anchors.

23. A soft tissue anchor device in accordance with claim 22 wherein the means for engaging and gathering soft tissue further comprises a sharp distal tip at a distal end of each of the at least two bone anchors.

* * * * *